US009821081B2

(12) United States Patent
Williams et al.

(10) Patent No.: US 9,821,081 B2
(45) Date of Patent: *Nov. 21, 2017

(54) PERFUME-FREE MALODOR REDUCING COMPOSITIONS

(71) Applicant: The Procter & Gamble Company, Cincinnati, OH (US)

(72) Inventors: Kristin Rhedrick Williams, West Chester, OH (US); Linda Magenis Girard, Union, KY (US); Ian Christopher Tholking, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 857 days.

This patent is subject to a terminal disclaimer.

(21) Appl. No.: 13/686,152

(22) Filed: Nov. 27, 2012

(65) Prior Publication Data

US 2014/0147408 A1    May 29, 2014

(51) Int. Cl.
  *A61L 9/01* (2006.01)
  *C11D 3/37* (2006.01)
  *A61L 2/22* (2006.01)
  *A61L 9/14* (2006.01)
  *C11D 3/00* (2006.01)
  *C11D 3/20* (2006.01)
  *C11D 3/22* (2006.01)

(52) U.S. Cl.
  CPC ............... *A61L 9/01* (2013.01); *A61L 2/22* (2013.01); *A61L 9/14* (2013.01); *C11D 3/0068* (2013.01); *C11D 3/2041* (2013.01); *C11D 3/2068* (2013.01); *C11D 3/222* (2013.01); *C11D 3/3723* (2013.01); *A61L 2202/25* (2013.01); *A61L 2202/26* (2013.01)

(58) Field of Classification Search
  None
  See application file for complete search history.

(56) References Cited

U.S. PATENT DOCUMENTS

| | | | |
|---|---|---|---|
| 5,670,475 A * | 9/1997 | Trinh et al. | 510/470 |
| 6,001,342 A | 12/1999 | Forestier et al. | |
| 6,103,687 A | 8/2000 | Cody et al. | |
| 6,454,876 B1 | 9/2002 | Ochomogo et al. | |
| 6,503,413 B2 | 1/2003 | Uchiyama et al. | |
| 6,653,274 B1 | 11/2003 | Godfroid et al. | |
| 6,680,289 B1 | 1/2004 | Woo et al. | |
| 6,833,342 B2 | 12/2004 | Woo et al. | |
| 2005/0084474 A1 | 4/2005 | Wu et al. | |
| 2008/0032912 A1* | 2/2008 | Warr et al. | 512/1 |
| 2010/0132741 A1 | 6/2010 | Frey et al. | |
| 2010/0249006 A1 | 9/2010 | Geret et al. | |
| 2011/0070181 A1* | 3/2011 | Williams et al. | 424/76.1 |
| 2011/0070182 A1 | 3/2011 | Williams | |
| 2012/0183488 A1 | 7/2012 | Woo et al. | |
| 2013/0136712 A1 | 5/2013 | Woo et al. | |

FOREIGN PATENT DOCUMENTS

| | | |
|---|---|---|
| JP | H03146064 A | 6/1991 |
| JP | 2002-113083 A | 4/2002 |
| JP | 2006-325669 A | 12/2006 |
| JP | 2007332130 A | 12/2007 |
| WO | WO 82/01993 | 6/1982 |
| WO | 03/033636 A1 | 4/2003 |
| WO | 2005/108541 A1 | 11/2005 |
| WO | WO 2012/097034 A1 | 7/2012 |

OTHER PUBLICATIONS

Iban Eduardo, Giorgiana Chietera, Daniele Bassi, Laura Rossini, and Alberto Vecchietti. Identification of key odor volatile compounds in the essential oil of nine peach accessions. J Sci Food Agric 2010: 90. 1146-1154.*
"Tetradecanal", fact sheet from the Good Scents Company, Downloaded Sep. 26, 2015 from the website: http://www.thegoodscentscompany.com/data/rw1000161.html.*
AzoNobel Functional Chemicals Chelates, Dissolvine GL Technical brochure, Apr. 2010.
Database WPI, Week 200809, Thomson Scientific, London, GB AN 2008-B34608 XP002631068.
The Good Scents Company, "9-octadecen-1-al", http://www.thegoodscentscompany.com/docs/doc1051261.html; 2 pages; downloaded Jul. 3, 2014.
The Good Scents Company, "beta-sinensal". http://www.thegoodscentscompany.com/docs/doc1051261.html; 2 pages; downloaded Jul. 3, 2014.
The Good Scents Company, "mimosa heptanal", http://www.thegoodscentscompany.com/docs/doc1051261.html; 2 pages; downloaded Jul. 3, 2014.
The Good Scents Company, "tetradecanal", http://www.thegoodscentscompany.com/docs/doc1051261.html; 2 pages; downloaded Jul. 3, 2014.
The Good Scents Company, "2-tetradecen-1-al", http://www.thegoodscentscompany.com/docs/doc1051261.html; 2 pages; downloaded Jul. 3, 2014.
The Good Scents Company, "(E)-2-tetradecen-1-al", http://www.thegoodscentscompany.com/docs/doc1051261.html; 2 pages; downloaded Jul. 3, 2014.
The Good Scents Company, "(Z)-8-tetradecen-1-al", http://www.thegoodscentscompany.com/docs/doc1051261.html; 2 pages; downloaded Jul. 3, 2014.
The Good Scents Company, "waxy aldehydes", http://www.thegoodscentscompany.com/docs/doc1051261.html; 2 pages; downloaded Jul. 3, 2014.
The Good Scents Company, "leerall", http://www.thegoodscentscompany.com/docs/doc1051261.html; 2 pages; downloaded Jul. 3, 2014.
The Good Scents Company, "green carbaldehyde", http://www.thegoodscentscompany.com/docs/doc1051261.html; 2 pages; downloaded Jul. 3, 2014.

(Continued)

*Primary Examiner* — Frederick Krass
*Assistant Examiner* — Michael P Cohen
(74) *Attorney, Agent, or Firm* — Abbey A. Lopez

(57) ABSTRACT

Perfume-free malodor reducing compositions comprising a malodor binding polymer and a malodor counteractant are provided. In some embodiments, the composition comprises a malodor binding polymer and GLDA. Such compositions may be used to reduce malodor on inanimate surfaces or in the air.

17 Claims, 4 Drawing Sheets

(56) References Cited

OTHER PUBLICATIONS

The Good Scents Company, "muguet undecadienal", http://www.thegoodscentscompany.com/docs/doc1051261.html; 2 pages; downloaded Jul. 3, 2014.
The Good Scents Company, "2-orris butanal", http://www.thegoodscentscompany.com/docs/doc1051261.html; 2 pages; downloaded Jul. 3, 2014.
The Good Scents Company, "2(1)-orris butanal", http://www.thegoodscentscompany.com/docs/doc1051261.html; 2 pages; downloaded Jul. 3, 2014.
The Good Scents Company, "trimethyl undecadienal", http://www.thegoodscentscompany.com/docs/doc1051261.html; 2 pages; downloaded Jul. 3, 2014.
PCT Search Report, International Application No. PCT/US2013/071373, dated Mar. 21, 2014, containing 25 pages.
Database WPI, Week 200143 Thomas Scientific, London, GB; AN 2001-400967 XP002721277.

* cited by examiner

PERFUME-FREE MALODOR REDUCING COMPOSITIONS

FIELD OF THE INVENTION

The present invention relates to perfume-free compositions that reduce malodors.

BACKGROUND OF THE INVENTION

Products for reducing malodors are well known in the art and are widely described in patent literature. Often times, such products incorporate scented perfumes, with or without other malodor control ingredients, to help mask malodors.

Products that are perfume-free and reduce malodor are desired by consumers as they may be considered more natural and discreet to use than products having perfume raw materials. In such case, manufacturers of perfume-free products for reducing malodors must rely solely on other malodor control ingredients or technologies (e.g. filters) to reduce malodors. However, when a malodor control product lacks a scented perfume, the consumer may not receive a sensory signal that the product is working, and the time required for the malodor control ingredient to reduce malodors may create consumer doubt as to the product's efficacy. Further, effectively controlling both amine-based malodors (e.g. fish and urine) and sulfur-based malodors (e.g. garlic and onion) may be difficult.

There remains a need for perfume-free compositions that quickly and effectively reduce a broad range of malodors.

SUMMARY OF THE INVENTION

The present invention relates to a perfume-free composition for reducing malodor. In one embodiment, there is provided a perfume-free composition for reducing malodor comprising an effective amount of a malodor binding polymer, an effective amount of a malodor counteractant, and an aqueous carrier, wherein the composition is essentially free of any material that would soil or stain fabric.

In another embodiment, there is provided a perfume-free composition for reducing malodor comprising an effective amount of a malodor binding polymer, about 0.15% to about 1%, by weight of said composition, of GLDA, an aqueous carrier, wherein the composition is essentially free of any material that would soil or stain fabric.

In yet another embodiment, there is provided an aqueous perfume-free composition for reducing malodor comprising about 0.01% to about 1%, by weight of said composition, of a homopolymeric polyethyleneimine having a molecular weight of 1,000 to 2,000,000, an effective amount of a glycol, about 0.15% to about 1%, by weight of said composition, of GLDA, about 90% to about 99.5% of an aqueous carrier, wherein the composition is essentially free of any material that would soil or stain fabric.

The present invention also relates to methods of reducing malodor comprising the steps of: contacting a malodor on a surface or in the air with an effective amount of a perfume-free malodor reducing composition comprising an effective amount of a malodor binding polymer, an effective amount of a malodor counteractant, and an aqueous carrier, wherein said composition is essentially free of any material that would soil or stain fabric.

DETAILED DESCRIPTION OF THE INVENTION

Figure 1:
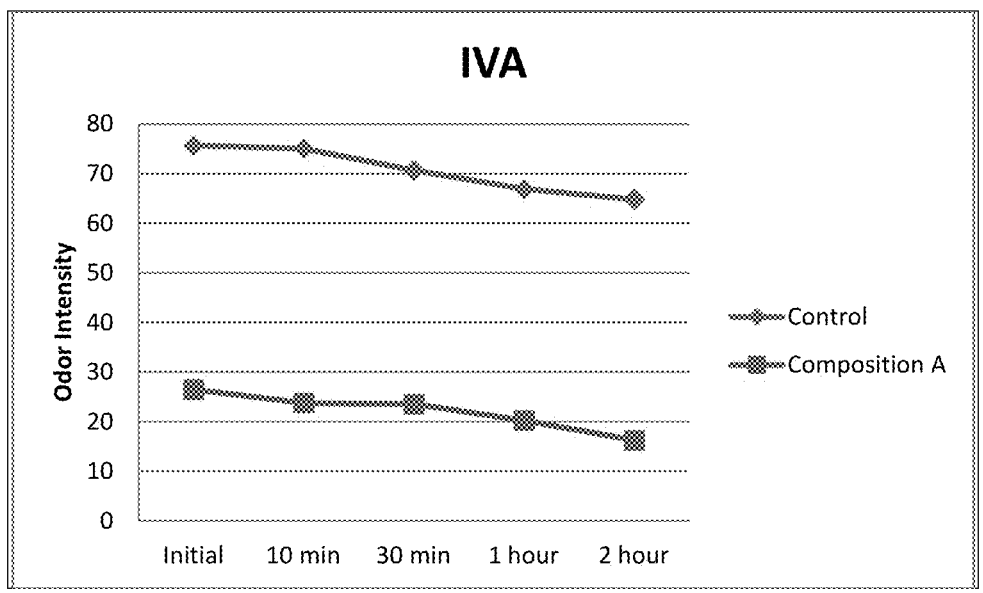
FIGS. 1-4 show the reduction of various malodors from fabrics treated with a perfume-free composition according to the present invention.
Figure 2:
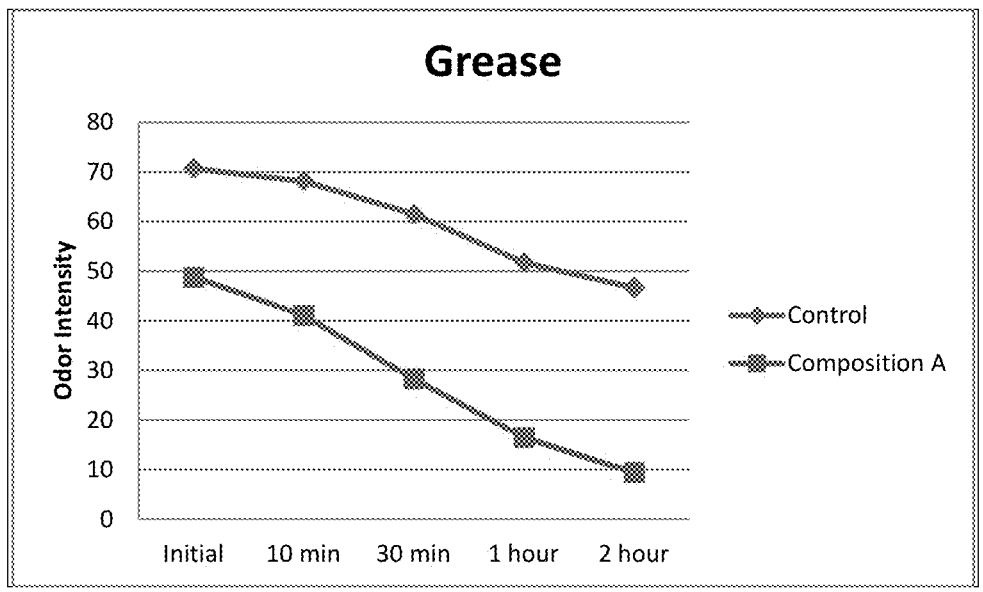
Figure 3:
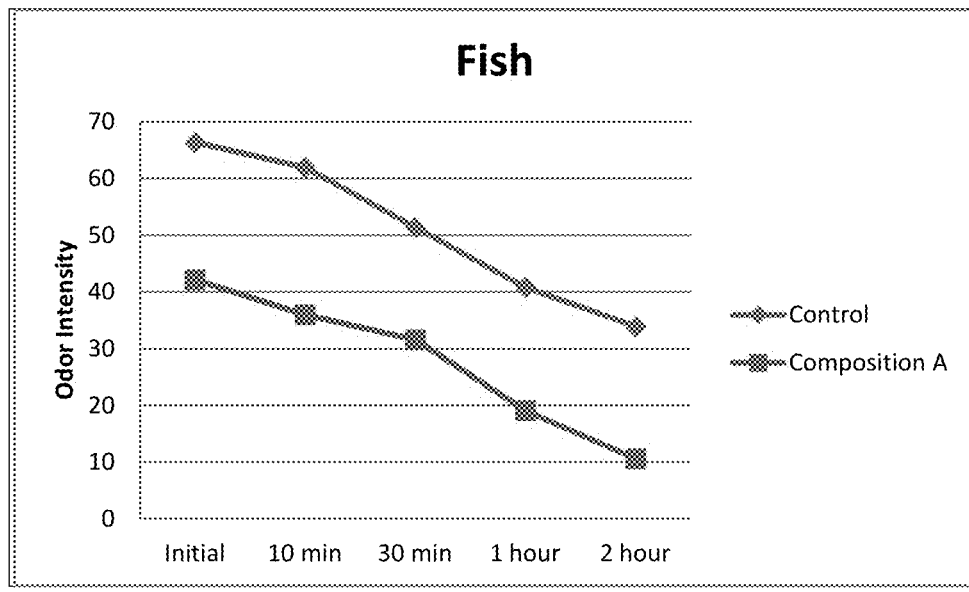
Figure 4:
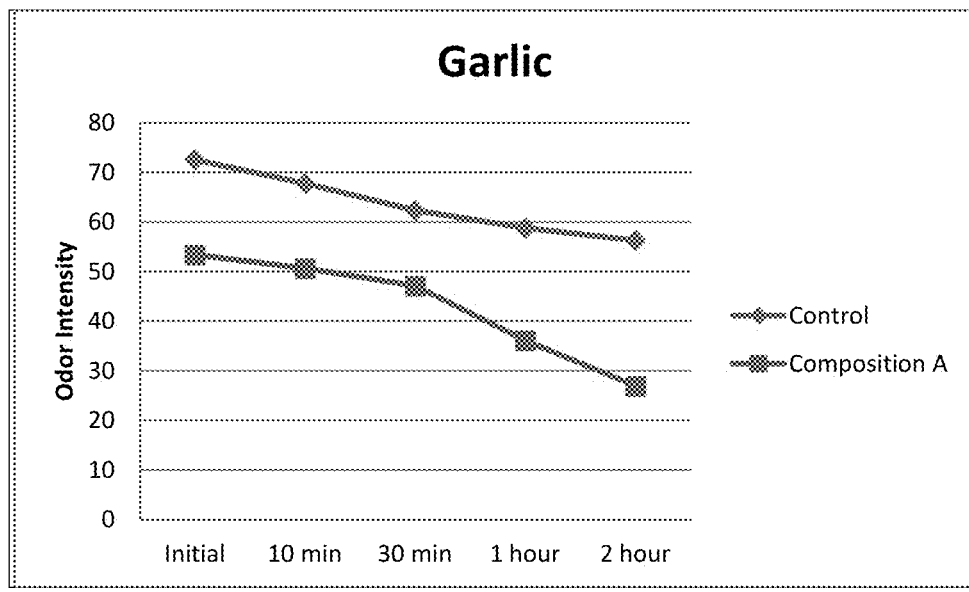

The present invention relates to a perfume-free composition for reducing malodor. A perfume refers to organic substances that are included in a product to provide a desired olfactory property, whether scented, low-scent/unscented. A perfume may include a single aromatic chemical or a mixture of aromatic chemicals. There are several aromatic chemicals, including ionones, hydrocarbons, alcohols, aldehydes, ketones, and esters. Exemplary perfume materials are disclosed in U.S. Pat. Nos. 5,663,134; 5,670,475; 5,783,544; 5,939,060; and 6,146,621.

The perfume-free composition and method of the present invention is designed to deliver genuine malodor reduction in the air or on inanimate surfaces, for example, fabrics contaminated with environmental malodors (e.g. odors from food, tobacco, perspiration). A genuine malodor reduction provides sensory and analytically measurable (e.g. gas chromatograph) malodor reduction. Thus, if the perfume-free composition delivers a genuine malodor reduction, the composition will neutralize malodors in the air and/or on fabrics. "Neutralize" or "neutralization" as used herein means chemically reacting with malodor components (e.g. the reaction of primary amines with aldehydes to form imines, reductive alkylation of amines, protonation and deprotonation of amines, polymerization or de-polymerization); or suppressing the volatility of malodorous components such that other parts of the composition may react (e.g. acid-base neutralization); or physically entrapping odorous molecules such that they are not re-released into the air (e.g. cyclodextrin inclusion complexes as described herein).

The perfume-free composition and method of the present invention does not leave fabrics susceptible to soiling and/or leave any unacceptable visible stains on fabrics. Compositions with high concentrations of malodor control ingredients (e.g. polymers and/or surfactants) can make fabrics susceptible to soiling and/or leave unacceptable visible stains on fabrics as the solution evaporates. Suitable amount of surfactants (e.g. solubilizer, wetting agent) in the composition is from about 0% to about 3% or no more than 3%, alternatively from about 0% to about 1% or no more than 1%, alternatively from about 0% to about 0.9% or no more than 0.9%, alternatively from about 0% to about 0.7 or no more than 0.7%, alternatively from about 0% to about 0.5% or no more than 0.5%, alternatively from about 0% to about 0.3% or no more than 0.3%, by weight of the composition.

I. Composition

The perfume-free composition of the present invention can comprise, consist of, or consist essentially of the elements and limitations of the invention described herein, as well any of the additional or optional ingredients, components, or limitations described herein.

A. Malodor Binding Polymer

The composition of the present invention includes a malodor binding polymer. A malodor binding polymer is polymer having an available functional group (e.g. amine) that has the affinity to neutralize malodor components. Monomers having an available function group with an affinity to neutralize malodor components are also contemplated. In the case of amine based compounds, the amine will have an affinity for aldehyde malodors. The amine may react with aldehyde malodors and form a new compound, such as an aminol, imine, or enamine which is not odorous.

A malodor binding polymer may include amine based compounds, such as monoamines, amino acids, polyethyleneimine polymers (PEIs), modified PEIs, substituted PEIs; acrylic acid polymers, such as polyacrylate co-polymer (e.g. Acumer™ 9000 from Rohm & Haas), polyacrylic acid polymers (e.g. Acusol™ from Rohm & Haas), and modified acrylate copolymers (e.g. Aculyn™ from Rohm & Haas); and modified methacrylate copolymers (e.g. HydroSal™ from Salvona Technologies); or mixtures thereof.

1. Amine Based Compounds

In some embodiments, the malodor binding polymer is an amine based compound with a molecular weight greater than 100 Daltons and at least 10% of its amine groups are primary amines. In one embodiment, the amine-based compound will be a polyamine with a molecular weight greater than 150 Daltons and 15% to 80% of its amine groups are primary amines. In another embodiment, the malodor binding polymer is an amine-based compound with a molecular weight greater than 1000 Daltons and from 0% to about 10% or less than 10% of its amine groups are primary amines.

A general structure for a primary amine compound useful in this invention is as follows:

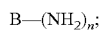

wherein B is a carrier material, and n is an index of value of at least 1. Suitable B carriers include both inorganic and organic carrier moieties. By "inorganic carrier", it is meant a carrier which is comprised of non- or substantially non-carbon based backbones.

Compounds containing a secondary amine group have a structure similar to the above with the exception that the compound comprises one or more —NH— groups as well as —NH$_2$ groups. The amine compounds of this general type may be relatively viscous materials.

Exemplary amine based compounds are those selected from monoamines, aminoaryl derivatives, polyamines and derivatives thereof, polyamino acids and copolymers thereof, glucamines, dendrimers, PEIs, substituted amines and amides monoamines, or mixtures thereof.

a. Monoamines

Monoamines may be utilized in the present invention. Nonlimiting examples of suitable monoamines for use in the present invention include, but are not limited to, primary amines that also contain hydroxy and/or alkoxy functional groups, such as the 2-hydroxyamines and/or 3-hydroxyamines; primary or secondary amines that also contain a functional group that enhances deposition of the monoamine compared to monoamines that lack that functional group, especially when the monoamine is interacting with the benefit agent. Primary monoamines may also be used herein in combination with secondary monoamines. However, sufficient levels of the primary monoamine must be used to provide at least 10% of the total amine groups within such combinations as primary amine groups.

b. Aminoaryl Derivatives

Exemplary aminoaryl derivatives are the amino-benzene derivatives including the alkyl esters of 4-amino benzoate compounds, ethyl-4-amino benzoate, phenylethyl-4-aminobenzoate, phenyl-4-aminobenzoate, 4-amino-N'-(3-aminopropyl)-benzamide, or mixtures thereof.

c. Polyamines

Examples of suitable amino functional polymers containing at least one primary amine group for the purposes of the present invention are:

Polyvinylamine with a MW of 300-2.10E6 Daltons (e.g Lupamine series 1500, 4500, 5000, 9000 available from BASF);

Polyvinylamine alkoxylated with a MW of ≥600 Daltons and a degree of ethoxylation of at least 0.5;

Polyvinylamine vinylalcohol-molar ratio 2:1, polyvinylaminevinylformamide-molar ratio 1:2 and polyvinylamine vinylformamide-molar ratio 2:1;

Triethylenetetramine, diethylenetriamine, tetraethylenepentamine;

Bis-aminopropylpiperazine;

amino substituted polyvinylalcohol with a MW ranging from 400-300,000 Daltons;

polyoxyethylene bis [amine] available from e.g. Sigma;

polyoxyethylene bis [6-aminohexyl] available from e.g. Sigma;

N,N'-bis-(3-aminopropyl)-1,3-propanediamine linear or branched (TPTA);

N,N'-bis-(3-aminopropyl)ethylenediamine;

bis (amino alkyl) alkyl diamine, linear or branched; and 1,4-bis-(3-aminopropyl) piperazine (BNPP).

d. Polyamino Acids

Suitable amine based compounds include polyamino acids. Polyamino acids are made up of amino acids or chemically modified amino acids. The amino acids may be selected from cysteine, histidine, isoleucine, tyrosine, tryptophane, leucine, lysine, glutamic acid, glutamine, glycine, alanine, aspartic acid, arginine, asparagine, phenylalanine, proline, serine, histidine, threonine, methionine, valine, and mixtures thereof. Amino acid derivatives may be tyrosine ethylate, glycine methylate, tryptophane ethylate, or mixtures thereof; homopolymers of amino acids; hydroxyamines; polyamino acids; or mixtures thereof.

In chemically modified amino acids, the amine or acidic function of the amino acid has reacted with a chemical reagent. This is often done to protect these chemical amine and acid functions of the amino acid in a subsequent reaction or to give special properties to the amino acids, like improved solubility. Examples of such chemical modifications are benzyloxycarbonyl, aminobutyric acid, butyl ester, and pyroglutamic acid. More examples of common modifications of amino acids and small amino acid fragments can be found in the Bachem, 1996, Peptides and Biochemicals Catalog.

One polyamino acid is polylysine, alternatively polylysines or polyamino acids where more than 50% of the amino acids are lysine, since the primary amine function in the side chain of the lysine is the most reactive amine of all amino acids. One polyamino acid has a molecular weight of 500 to 10,000,000, alternatively between 2000 and 25,000.

The polyamino acid can be cross linked. The cross linking can be obtained for example by condensation of the amine group in the side chain of the amino acid like lysine with the carboxyl function on the amino acid or with protein cross linkers like PEG derivatives. The cross linked polyamino acids still need to have free primary and/or secondary amino groups left for neutralization. Cross linked polyamino acid has a molecular weight of 20,000 to 10,000,000; alternatively between 200,000 and 2,000,000.

The polyamino acid or the amino acid can be co-polymerized with other reagents like for instance with acids, amides, acyl chlorides, aminocaproic acid, adipic acid, ethylhexanoic acid, caprolactam, or mixtures thereof. The molar ratio used in these copolymers ranges from 1:1

(reagent/amino acid (lysine)) to 1:20, alternatively from 1:1 to 1:10. The polyamino acid like polylysine can be unethoxylated or partially ethoxylated so long as the requisite amount of primary amine remains in the polymer.

e. Dendrimers

Also useful amine based compounds are polypropylenimine dendrimers and the commercially available Starburst® polyamidoamines (PAMAM) dendrimers, generation G0-G10 from Dendritech and the dendrimers Astromols®, generation 1-5 from DSM being DiAminoButane PolyAmine DAB (PA)x dendrimers with x=2ⁿ×4 and n being generally comprised between 0 and 4.

f. PEIs

In one embodiment, the malodor binding polymer is a PEI. It has been surprisingly discovered that amine based polymers at a pH of about 4 to about 8, alternatively above 5 to about 8, alternatively 7 can neutralize amine based odors. PEIs have the following general formula:

—(CH2-CH2-NH)n-;n=10-105

Homopolymeric PEIs are branched, spherical polyamines with a well defined ratio of primary, secondary and tertiary amine functions. They are best described in the following partial structural formula:

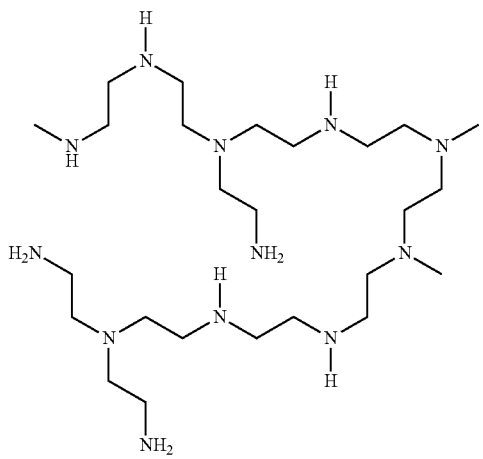

The chemical structure of homopolymeric PEIs follows a simple principle: one amine function-two carbons.

The composition may comprise a homopolymeric polyethylenimine having a molecular weight of about 800 to about 2,000,000, alternatively about 1,000 to about 2,000,000, alternatively about 1,200 to about 25,000, alternatively about 1,300 to about 25,000, alternatively about 2,000 to about 25,000, alternatively about 10,000 to about 2,000,000, alternatively about 25,000 to about 2,000,000, alternatively about 25,000. Exemplary homopolymeric PEIs include those that are commercially available under the tradename Lupasol® from BASF. Lupasol products are usually obtained through polymerization of the ethylenimine monomer. The ethylenimine monomer has totally reacted in the polymer matrix. Suitable Lupasol products include Lupasol FG (MW 800), G20wfv (MW 1300), PR8515 (MW 2000), WF (MW 25,000), FC (MW 800), G20 (MW 1300), G35 (MW 1200), G100 (MW 2000), HF (MW 25,000), P (MW 750,000), PS (MW 750,000), SK (MW 2,000,000), SNA (MW 1,000,000).

In some embodiments, the composition comprises Lupasol HF or WF (MW 25,000), P (MW 750,000), PS (MW 750,000), SK (MW 2,000,000), 620wfv (MW 1300) or PR 1815 (MW 2000), or Epomin SP-103, Epomin SP-110, Epomin SP-003, Epomin SP-006, Epomin SP-012, Epomin SP-018, Epomin SP-200, or partially alkoxylated PEI, like PEI 80% ethoxylated from Aldrich. In one embodiment, the composition contains Lupasol WF (MW 25,000).

Also suitable amine based compounds for use in the composition are modified PEIs, partially alkylated polyethylene polymers, PEIs with hydroxyl groups, 1,5-pentanediamine, 1,6-hexanediamine, 1,3 pentanediamine, 3-dimethylpropanediamine, 1,2-cyclohexanediamine, 1,3-bis (aminomethyl)cyclohexane, tripropylenetetraamine, bis (3-aminopropyl)piperazine, dipropylenetriamine, tris(2-aminoethylamine), tetraethylenepentamine, bishexamethylenetriamine, bis(3-aminopropyl) 1,6-hexamethylenediamine, 3,3'-diamino-N-methyldipropylamine, 2-methyl-1,5-pentanediamine, N,N,N',N'-tetra(2-aminoethyl) ethylenediamine, N,N,N',N'-tetra(3-aminopropyl)-1,4-butanediamine, pentaethylhexamine, 1,3-diamino-2-propyl-tert-butylether, isophorondiamine, 4,4',-diaminodicyclohylmethane, N-methyl-N-(3-aminopropyl) ethanolamine, spermine, spermidine, 1-piperazineethaneamine, 2-(bis(2-aminoethyl)amino)ethanol, ethoxylated N-(tallowalkyl)trimethylene diamines, poly [oxy(methyl-1,2-ethanediyl)], α-(2-aminomethyl-ethoxy)- (=C.A.S No. 9046-10-0); poly[oxy(methyl-1,2-ethanediyl)], α-hydro-)-ω-(2-aminomethylethoxy)-, ether with 2-ethyl-2-(hydroxymethyl)-1,3-propanediol (=C.A.S, No. 39423-51-3); commercially available under the tradename Jeffamines T-403, D-230, D-400, D-2000; 2,2',2"-triaminotriethylamine; 2,2'-diamino-diethylamine; 3,3'-diamino-dipropylamine, 1,3 bis aminoethyl-cyclohexane commercially available from Mitsubishi, and the C12 Sternamines commercially available from Clariant like the C12 Sternamin(propylenamine)ₙ with n=¾.

In one embodiment, the malodor binding polymer may be used in an effective amount to provide a reduction of microbes on fabric and/or in the air. When using a malodor binding polymer, an effective amount reduces microbes by at least 1 log difference as compared to a composition lacking the malodor binding polymer. This difference is then attributed to the use of the malodor binding polymer and not the inherent variability in the microbial species.

Suitable levels of malodor binding polymer are from about 0.01% to about 2%, alternatively from about 0.01% to about 1%, alternatively about 0.01% to about 0.8%, alternatively about 0.01% to about 0.6%, alternatively about 0.01% to about 0.1%, alternatively about 0.01% to about 0.07%, alternatively about 0.07%, by weight of the composition. Compositions with higher amount of malodor binding polymer may make fabrics susceptible to soiling and/or leave unacceptable visible stains on fabrics as the solution evaporates off of the fabric.

B. Malodor Counteractants

The composition may utilize one or more malodor counteractants. Malodor counteractants may include components which lower the vapor pressure of odorous compounds, solubilize malodor compounds, physically entrap odors (e.g. flocculate or encapsulate), physically bind odors, or physically repel odors from binding to inanimate surfaces. When used in combination with the malodor binding polymer, the composition may neutralize a broader range of malodor causing materials which, in turn, further reduces malodors in the air or on inanimate surfaces.

1. Low Molecular Weight Polyols

Low molecular weight polyols with relatively high boiling points, as compared to water, such as ethylene glycol, diethylene glycol (DEG), triethylene glycol, propylene glycol, dipropylene glycol, and/or glycerine may be utilized as a malodor counteractant for improving malodor reduction.

The glycol used in the composition of the present invention may be glycerine, ethylene glycol, propylene glycol, dipropylene glycol, polyethylene glycol, propylene glycol methyl ether, propylene glycol phenyl ether, propylene glycol methyl ether acetate, propylene glycol n-butyl ether, dipropylene glycol n-butyl ether, dipropylene glycol n-propyl ether, ethylene glycole phenyl ether, DEG n-butyl ether, dipropylene glycol n-butyl ether, DEG mono butyl ether, dipropylene glycol methyl ether, tripropylene glycol methyl ether, tripropylene glycol n-butyl ether, other glycol ethers, or mixtures thereof. In one embodiment, the glycol used is ethylene glycol, propylene glycol, or mixtures thereof. In another embodiment, the glycol used is DEG.

Typically, the low molecular weight polyol is added to the composition of the present invention at a level of from about 0.01% to about 5%, by weight of the composition, alternatively from about 0.05% to about 1%, alternatively from about 0.1% to about 0.5%, by weight of the composition. Compositions with higher concentrations may make fabrics susceptible to soiling and/or leave unacceptable visible stains on fabrics as the solution evaporates off of the fabric. The weight ratio of low molecular weight polyol to the malodor binding polymer is from about 500:1 to about 4:1, alternatively from about 1:100 to about 25:1, alternatively from about 1:50 to about 4:1, alternatively about 4:1.

2. Cyclodextrin

In some embodiments, the composition may include solubilized, water-soluble, uncomplexed cyclodextrin. As used herein, the term "cyclodextrin" includes any of the known cyclodextrins such as unsubstituted cyclodextrins containing from six to twelve glucose units, especially, alpha-cyclodextrin, beta-cyclodextrin, gamma-cyclodextrin and/or their derivatives and/or mixtures thereof. The alpha-cyclodextrin consists of six glucose units, the beta-cyclodextrin consists of seven glucose units, and the gamma-cyclodextrin consists of eight glucose units arranged in a donut-shaped ring. The specific coupling and conformation of the glucose units give the cyclodextrins a rigid, conical molecular structure with a hollow interior of a specific volume. The "lining" of the internal cavity is formed by hydrogen atoms and glycosidic bridging oxygen atoms, therefore this surface is fairly hydrophobic. The unique shape and physical-chemical property of the cavity enable the cyclodextrin molecules to absorb (form inclusion complexes with) organic molecules or parts of organic molecules which can fit into the cavity.

Cyclodextrin molecules are described in U.S. Pat. No. 5,714,137, and U.S. Pat. No. 5,942,217. Suitable levels of cyclodextrin are from about 0.1% to about 5%, alternatively from about 0.2% to about 4%, alternatively from about 0.3% to about 3%, alternatively from about 0.4% to about 2%, by weight of the composition. Compositions with higher concentrations can make fabrics susceptible to soiling and/or leave unacceptable visible stains on fabrics as the solution evaporates off of the fabric. The latter is especially a problem on thin, colored, synthetic fabrics. In order to avoid or minimize the occurrence of fabric staining, the fabric may be treated at a level of less than about 5 mg of cyclodextrin per mg of fabric, alternatively less than about 2 mg of cyclodextrin per mg of fabric.

C. Buffering Agent

The composition of the present invention includes a buffering agent. A buffer may be sterically stable, and used in this composition solely for maintaining the desired pH. The composition may have a pH from about 3 to about 8, alternatively from about 4 to about 7, alternatively from about 5 to about 8, alternatively from about 6 to about 8, alternatively about 6 to about 7, alternatively about 7, alternatively about 6.5.

The buffer can be alkaline, acidic or neutral. Suitable buffers may include a dibasic acid, carboxylic acid, a dicarboxylic acid like maleic acid, glutamic acid diacetic acid (GLDA), triethanolamine, or mixtures thereof. A suitable commercially available GLDA is Dissolvine™ GL-47 from AkzoNobel. The compositions may contain about 0.15% to about 1%, alternatively about 0.15% to about 0.5%, by weight of the composition, of GLDA.

Other suitable buffering agents for compositions of this invention include biological buffering agents. Some examples are nitrogen-containing materials, sulfonic acid buffers like 3-(N-morpholino)propanesulfonic acid (MOPS) or N-(2-Acetamido)-2-aminoethanesulfonic acid (ACES), which have a near neutral 6.2 to 7.5 pKa and provide adequate buffering capacity at a neutral pH. Other examples are amino acids such as lysine or lower alcohol amines like mono-, di-, and tri-ethanolamine. Other nitrogen-containing buffering agents are tri(hydroxymethyl)amino methane ($(HOCH_2)_3CNH_3$) (TRIS), 2-amino-2-ethyl-1,3-propanediol, 2-amino-2-methyl-propanol, 2-amino-2-methyl-1,3-propanol, disodium glutamate, N-methyl diethanolamide, 2-dimethylamino-2-methylpropanol (DMAMP), 1,3-bis(methylamine)-cyclohexane, 1,3-diamino-propanol N,N'-tetra-methyl-1,3-diamino-2-propanol, N,N-bis(2-hydroxyethyl)glycine (bicine) and N-tris (hydroxymethyl)methyl glycine (tricine). Mixtures of any of the above are also acceptable.

The composition may comprise at least about 0.001%, alternatively at least about alternatively at least about 0.01%, alternatively from about 0.01% to about 0.1%, by weight of the composition, of a buffering agent. The composition may also contain no more than about 1%, alternatively no more than about 0.75%, alternatively no more than about 0.5%, by weight of the composition, of a buffering agent.

Carboxylic acids such as citric acid may act as metal ion chelants and can form metallic salts with low water solubility. As such, in some embodiments, the composition is essentially free of citric acids, meaning the composition comprises less than about 0.05%, alternatively less than about 0.03%, alternatively less than about 0.015%, by weight of the composition, of citric acid.

D. Solubilizer

The composition of the present invention may contain a solubilizing aid to solubilize any excess hydrophobic organic materials which may be added to the composition. A suitable solubilizing aid is a surfactant, such as a no-foaming or low-foaming surfactant. Suitable surfactants are nonionic surfactants, cationic surfactants, amphoteric surfactants, zwitterionic surfactants, and mixtures thereof.

In some embodiments, the composition contains nonionic surfactants, cationic surfactants, and mixtures thereof. In one embodiment, the composition contains hydrogenated castor oil. One suitable hydrogenated castor oil (HCO) that may be used in the present composition is Basophor™, available from BASF.

Compositions containing anionic surfactants and/or detergent surfactants may make fabrics susceptible to soiling and/or leave unacceptable visible stains on fabrics as the solution evaporates off of the fabric. In some embodiments, the composition is free of anionic surfactants and/or detergent surfactants.

When the solubilizing agent is present, it is typically present at a level of from about 0.01% to about 3%, alternatively from about 0.05% to about 1%, alternatively less than about 0.5%, alternatively from about 0.01% to about 0.5%, by weight of the composition. Compositions with higher concentrations of solubilizer may make fabrics susceptible to soiling and/or leave unacceptable visible stains on fabrics as the solution evaporates off of the fabric.

E. Antimicrobial Compounds

The composition of the present invention may include an effective amount of a compound for reducing microbes in the air or on inanimate surfaces. Antimicrobial compounds are effective on gram negative and gram positive bacteria and fungi typically found on indoor surfaces that have contacted human skin or pets such as couches, pillows, pet bedding, and carpets. Such microbial species include *Klebsiella pneumoniae, Staphylococcus aureus, Aspergillus niger, Klebsiella pneumoniae, Steptococcus pyogenes, Salmonella choleraesuis, Escherichia coli, Trichophyton mentagrophytes,* and *Pseudomonoas aeruginosa.* In some embodiments, the antimicrobial compounds are also effective on viruses such H1-N1, Rhinovirus, Respiratory Syncytial, Poliovirus Type 1, Rotavirus, Influenza A, Herpes simplex types 1 & 2, Hepatitis A, and Human Coronavirus.

Antimicrobial compounds suitable in the composition of the present invention can be any organic material which will not cause damage to fabric appearance (e.g., discoloration, coloration such as yellowing, bleaching). Water-soluble antimicrobial compounds include organic sulfur compounds, halogenated compounds, cyclic organic nitrogen compounds, low molecular weight aldehydes, quaternary compounds, dehydroacetic acid, phenyl and phenoxy compounds, or mixtures thereof.

In one embodiment, a quaternary compound is used. Examples of commercially available quaternary compounds suitable for use in the composition is Barquat available from Lonza Corporation; and didecyl dimethyl ammonium chloride quat under the trade name Bardac® 2250 from Lonza Corporation.

The antimicrobial compound may be present in an amount from about 500 ppm to about 7000 ppm, alternatively about 1000 ppm to about 5000 ppm, alternatively about 1000 ppm to about 3000 ppm, alternatively about 1400 ppm to about 2500 ppm, by weight of the composition.

F. Preservatives

The composition of the present invention may include a preservative. The preservative is included in the present invention in an amount sufficient to prevent spoilage or prevent growth of inadvertently added microorganisms for a specific period of time, but not sufficient enough to contribute to the odor neutralizing performance of the composition. In other words, the preservative is not being used as the antimicrobial compound to kill microorganisms on the surface onto which the composition is deposited in order to eliminate odors produced by microorganisms. Instead, it is being used to prevent spoilage of the composition in order to increase the shelf-life of the composition.

The preservative can be any organic preservative material which will not cause damage to fabric appearance, e.g., discoloration, coloration, bleaching. Suitable water-soluble preservatives include organic sulfur compounds, halogenated compounds, cyclic organic nitrogen compounds, low molecular weight aldehydes, parabens, propane diaol materials, isothiazolinones, quaternary compounds, benzoates, low molecular weight alcohols, dehydroacetic acid, phenyl and phenoxy compounds, or mixtures thereof.

Non-limiting examples of commercially available water-soluble preservatives for use in the present invention include a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Co.; 5-bromo-5-nitro-1,3-dioxane, available under the tradename Bronidox L® from Henkel; 2-bromo-2-nitropropane-1,3-diol, available under the trade name Bronopol® from Inolex; 1,1'-hexamethylene bis(5-(p-chlorophenyl)biguanide), commonly known as chlorhexidine, and its salts, e.g., with acetic and digluconic acids; a 95:5 mixture of 1,3-bis(hydroxymethyl)-5,5-dimethyl-2,4-imidazolidinedione and 3-butyl-2-iodopropynyl carbamate, available under the trade name Glydant Plus® from Lonza; N-[1,3-bis(hydroxymethyl)2,5-dioxo-4-imidazolidinyl]-N,N'-bis(hydroxy-methyl) urea, commonly known as diazolidinyl urea, available under the trade name Germall® II from Sutton Laboratories, Inc.; N,N"-methylenebis{N'-[1-(hydroxymethyl)-2,5-dioxo-4-imidazolidinyl]urea}, commonly known as imidazolidinyl urea, available, e.g., under the trade name Abiol® from 3V-Sigma, Unicide U-13® from Induchem, Germall 115® from Sutton Laboratories, Inc.; polymethoxy bicyclic oxazolidine, available under the trade name Nuosept® C from Hüls America; glutaraldehyde; polyaminopropyl biguanide, available under the trade name Cosmocil CQ® from ICI Americas, Inc., or under the trade name Mikrokill® from Brooks, Inc; dehydroacetic acid; and benzsiothiazolinone available under the trade name Koralone™ B-119 from Rohm and Hass Corporation.

Suitable levels of preservative are from about 0.0001% to about 0.5%, alternatively from about 0.0002% to about 0.2%, alternatively from about 0.0003% to about 0.1%, by weight of the composition.

G. Wetting Agent

The composition may include a wetting agent that provides a low surface tension that permits the composition to spread readily and more uniformly on hydrophobic surfaces like polyester and nylon. It has been found that the aqueous solution, without such a wetting agent will not spread satisfactorily. The spreading of the composition also allows it to dry faster, so that the treated material is ready to use sooner. Furthermore, a composition containing a wetting agent may penetrate hydrophobic, oily soil better for improved malodor neutralization. A composition containing a wetting agent may also provide improved "in-wear" electrostatic control. For concentrated compositions, the wetting agent facilitates the dispersion of many actives such as antimicrobial actives in the concentrated aqueous compositions.

Nonlimiting examples of wetting agents include block copolymers of ethylene oxide and propylene oxide. Suitable block polyoxyethylene-polyoxypropylene polymeric surfactants include those based on ethylene glycol, propylene glycol, glycerol, trimethylolpropane and ethylenediamine as the initial reactive hydrogen compound. Polymeric compounds made from a sequential ethoxylation and propoxylation of initial compounds with a single reactive hydrogen atom, such as $C_{12-18}$ aliphatic alcohols, are not generally compatible with the cyclodextrin. Certain of the block polymer surfactant compounds designated Pluronic® and Tetronic® by the BASF-Wyandotte Corp., Wyandotte, Mich., are readily available.

Nonlimiting examples of cyclodextrin-compatible wetting agents of this type are described in U.S. Pat. No. 5,714,137 and include the Silwet surfactants available from Momentive Performance Chemical, Albany, N.Y. Exemplary Silwet surfactants are as follows:

| Name | Average MW |
|---|---|
| L-7608 | 600; |
| L-7607 | 1,000; |
| L-77 | 600; |
| L-7605 | 6,000; |
| L-7604 | 4,000; |
| L-7600 | 4,000; |
| L-7657 | 5,000; |
| L-7602 | 3,000; | and mixtures thereof.

H. Aqueous Carrier

The composition of the present invention may include an aqueous carrier. The aqueous carrier which is used may be distilled, deionized, or tap water. Water may be present in any amount for the composition to be an aqueous solution. In some embodiments, water may be present in an amount of about 85% to 99.5%, alternatively about 90% to about 99.5%, alternatively about 92% to about 99.5%, alternatively about 95%, by weight of said composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the composition of the present invention due to the addition of these alcohols to such things as stabilizers for some preservatives, the level of monohydric alcohol may be less than about 5%, alternatively less than about 3%, alternatively less than about 1%, alternatively from about 0.5% to about 3%, by weight of the composition.

I. Other Optional Ingredients

Adjuvants can be optionally added to the composition herein for their known purposes. Such adjuvants include, but are not limited to, water soluble metallic salts, antistatic agents, insect and moth repelling agents, colorants, antioxidants, and mixtures thereof.

II. Method of Making

The perfume-free composition of the present invention can be made in any suitable manner known in the art. All of the ingredients can simply be mixed together. In certain embodiments, it may be desirable to make a concentrated mixture of ingredients and dilute by adding the same to an aqueous carrier before dispersing the composition into the air or on an inanimate surface. In another embodiment, the malodor binding polymer may be dispersed in one vessel containing deionized water and ethanol, and low molecular polyols. To this vessel, then, the buffer is added until fully dispersed and visually dissolved. In a separate vessel, the solubilizer and any hydrophobic materials are mixed until homogenous and then added to the first mixing vessel, and mixed until homogenous.

III. Methods of Use

The perfume-free composition of the present invention can be used by dispersing, e.g., by placing the aqueous solution into a dispensing means, such as a spray dispenser and spraying an effective amount into the air or onto the desired surface or article. An effective amount as defined herein means an amount sufficient to neutralize malodor to the point that it is not discernible by the human sense of smell yet not so much as to saturate or create a pool of liquid on an article or surface and so that, when dry, there is no visual deposit readily discernible. Dispersing can be achieved by using a spray device, a roller, a pad, etc.

The present invention encompasses the method of dispersing an effective amount of the composition for reducing malodor onto household surfaces. The household surfaces are selected from the group consisting of countertops, cabinets, walls, floors, bathroom surfaces, and kitchen surfaces.

The present invention encompasses the method of dispersing a mist of an effective amount of the composition for reducing malodor onto fabric and/or fabric articles. The fabric and/or fabric articles include, but are not limited to, clothes, curtains, drapes, upholstered furniture, carpeting, bed linens, bath linens, tablecloths, sleeping bags, tents, car interior, e.g., car carpet, fabric car seats, etc.

The present invention encompasses the method of dispersing a mist of an effective amount of the composition for reducing malodor impression onto and into shoes wherein the shoes are not sprayed to saturation.

The present invention encompasses the method of dispersing a mist of an effective amount of the composition for reducing malodor impression onto shower curtains.

The present invention relates to the method of dispersing a mist of an effective amount of the composition for reducing malodor impression onto and/or into garbage cans and/or recycling bins.

The present invention relates to the method of dispersing a mist of an effective amount of the composition for reducing malodor impression into the air to neutralize malodor.

The present invention relates to the method of dispersing a mist of an effective amount of the composition for reducing malodor impression into and/or onto major household appliances including, but not limited to, refrigerators, freezers, washing machines, automatic dryers, ovens, microwave ovens, dishwashers, etc., to neutralize malodor.

The present invention relates to the method of dispersing a mist of an effective amount of the composition for reducing malodor impression onto cat litter, pet bedding and pet houses to neutralize malodor.

The present invention relates to the method of dispersing a mist of an effective amount of the composition for reducing malodor impression onto household pets to neutralize malodor.

EXAMPLES

Malodor Reduction

Table 1 shows non-limiting examples of perfume-free compositions according to the present invention.

TABLE 1

| | Composition A | Composition B | Composition C | Composition D |
|---|---|---|---|---|
| Deionized Water | 95.648 | 95.835 | 95.390 | 96.990 |
| Ethanol | 3.000 | 3.000 | 3.000 | 1.500 |
| Lupasol HF | 0.053 | 0.065 | 0.065 | 0.065 |
| Diethylene Glycol | 0.175 | 0.175 | 0.175 | 0.250 |
| Silwet L-7600 | 0.100 | 0.100 | 0.100 | 0.100 |
| Uniquat 2250 | 0.060 | 0.060 | 0.060 | 0.060 |
| Maleic Acid | 0.050 | 0.050 | 0.050 | 0.050 |
| Citric Acid | 0.015 | 0.015 | 0.015 | 0.015 |
| Koralone | 0.015 | 0.015 | 0.015 | 0.015 |
| HCO | 0.250 | 0.050 | 0 | 0.050 |
| Hydroxypropyl Beta CD | 0.630 | 0.630 | 0.630 | 0.900 |
| Sodium Hydroxide *adjust to 6.8 | 0.005* | 0.005* | 0.500* | 0.005* |
| Total | 100 | 100 | 100 | 100 |

Malodor Reduction—Sensory Test

For each malodor (isovaleric acid (IVA) to represent body odor, grease, fish, and garlic), two fabric swatches (polyester-cotton blend) are exposed to a specific malodor of interest. For grease infusion, place 8 ounces of grease in a Presto™ electric skillet and cover with the skillet lid. Place the skillet in a 30 gallon metal garbage can. Run the electric cord from the skillet through a 1.5 inch hole in the garbage can. Heat the skillet to 121° C. and allow it to equilibrate for 15 minutes. Remove the lid. Suspend 8 inch by 8 inch fabric swatches from the metal clips on a carousel in the garbage can lid. Measured from the bottom of the swatches, the distance to the top of the skillet is 8 inches. Place lid on garbage can and manually turn the carousel 15 rotations per minute for a period of 40 minutes such that the odor grade is about 60 to about 80. Repeat the malodor infusion steps for garlic odor using 0.63 g chopped garlic per swatch; for fish odor using 12.5 g of fish per swatch; and about 1.1 ul of IVA per swatch.

Composition A in Table 1 is prepared and one malodor infused fabric swatch for each malodor is sprayed, from a distance of 6 inches, with Composition A. The spray consists of two full strokes of the trigger sprayer bottle. One malodor infused fabric swatch for each malodor is left untreated to confirm malodor contamination and to represent a control. After treatment, the treated fabric swatches are placed on a garment rack.

Trained panelists in assigned groups evaluate all the treated and untreated fabric swatches for designated attribute e.g. perfume intensity for the initial time point. A panel leader or assistant presents the swatches to the panelists in the order they are to be evaluated; this is randomized each time. Panelists are required to wait approximately 10 seconds between evaluations. Panelists mark their ballots by evaluating the attribute on a 0-100 scale.

| | |
|---|---|
| 0 | No Perfume Present |
| 10 | I think there is perfume present (unsure) |
| 20 | I detect something, but can I recognize it? |
| 25 | Slight perfume present |
| 50 | Moderate perfume present |
| 75 | Strong perfume present |
| 100 | Extremely strong perfume present |

A clean swatch is used to clear the nose and is not given a malodor intensity grade. Panelists repeat the procedure above at specified time points: initial (i.e. within 2 minutes of treatment), 10 minutes, 30 minutes, 1 hour and 2 hours after initial spray. The panelists' grade for each time point is then averaged.

The resulting malodor odor intensity grades are recorded and plotted in FIGS. 1-4. The malodor control is also plotted to show the level of malodor present without treatment. For each malodor, at least 50% of the malodor is reduced within minutes of spraying with Composition A of the present invention.

Malodor Reduction—Analytical Test

Compositions B, C, and D are prepared in accordance with Table 1. Four fabric swatches are contaminated with bacon grease odor, as outlined in the above Sensory Test. Three of the four fabric swatches are sprayed with Compositions B, C, and D; one fabric swatch for each of Compositions B, C, and D. The remaining fabric swatch is sprayed with a Control composition shown in Table 2.

TABLE 2

| Control | |
|---|---|
| DI Water | Balance |
| Ethanol | 3.000 |
| Lupasol HF | 0.053 |
| Diethylene Glycol | 0.175 |
| Silwet L-7600 | 0.100 |
| Uniquat 2250 | 0.060 |
| Maleic Acid | 0.050 |
| Citric Acid | 0.015 |
| Koralone | 0.015 |
| Perfume | 0.670 |
| HCO | 0.05 |
| Hydroxypropyl Beta CD | 0.630 |
| Sodium Hydroxide | 0.005 |
| Total | 100 |

The spray for each swatch consists of two full strokes of the trigger sprayer bottle. The bottle is held 6 inches away from the fabric and the spray is centered on the fabric. Immediately after spraying, each swatch is cut in half, rolled, and each is placed into a 125 mL headspace vial. The vials are sealed and then analyzed by sampling each vial using a PDMS SPME fiber and analyzed by GC/MS. Malodor components, previously identified, are then tracked through all the samples. A reading of malodor molecules is recorded within 10 minutes (represented by "0" in FIG. 5) and again after 2 hours (after the vials have equilibrated at 100° C.). Data is compiled of total area count of the cumulative area counts of the individual peaks.

Figure 5:
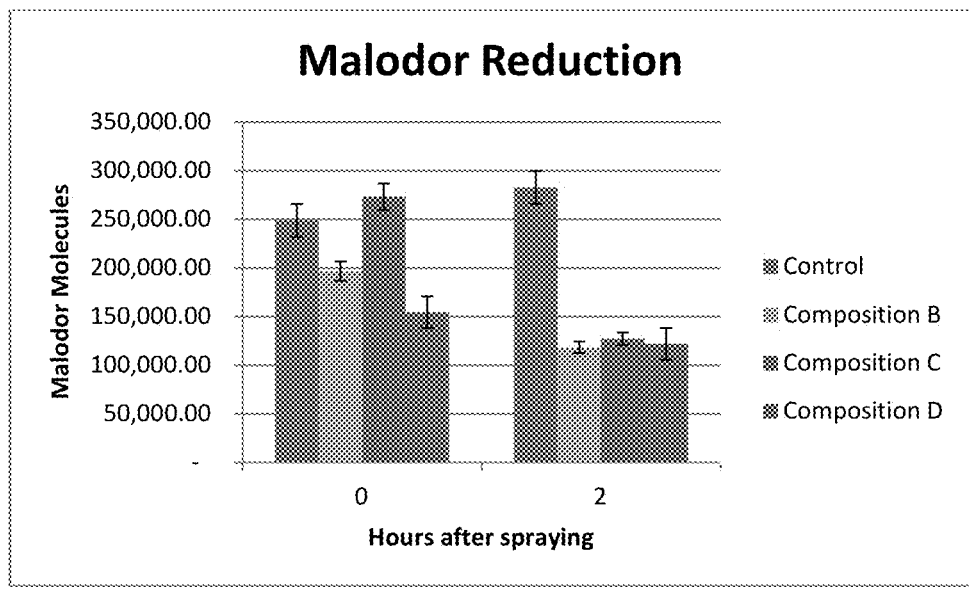
FIG. 5 shows the reduction of malodor molecules from fabrics treated with perfume-free compositions according to the present invention.

FIG. 5 shows that Compositions B, C, and D provide genuine malodor removal by chemically reacting with the malodor molecules and not masking the malodor. Surprisingly, Compositions B, C, and D removed more malodor than the Control composition which contained perfume and all the same ingredients as B, C, and D.

Malodor Removal Capacity—Reserve Alkalinity

A sample solution for each of Compositions E, F, G, and H, according to Table 3, is prepared by the operator. 100 mls of each composition is poured and vigorously mixed in a beaker. When the pH measurement of the solution is stabilized, the solution is titrated (with butylamine for reserve alkalinity and butyric acid for reserve acidity) until the solution reaches the desired pH.

When titrating to a pH of 9.5, calculate percent of reserve alkalinity (% RA) as shown below:

$$\% \ RA = \frac{mls \ \text{butyric acid} \times \text{normality of butyric acid} \times 40 \times 100}{\text{sample wt(g)} \times 1000}$$

When titrating to a pH of 4.5, calculate % RA as shown below:

$$\% \ RA = \frac{mls \ \text{butylamine} \times \text{normality of butylamine} \times 40 \times 100}{\text{sample wt(g)} \times 1000}$$

Figure 6:
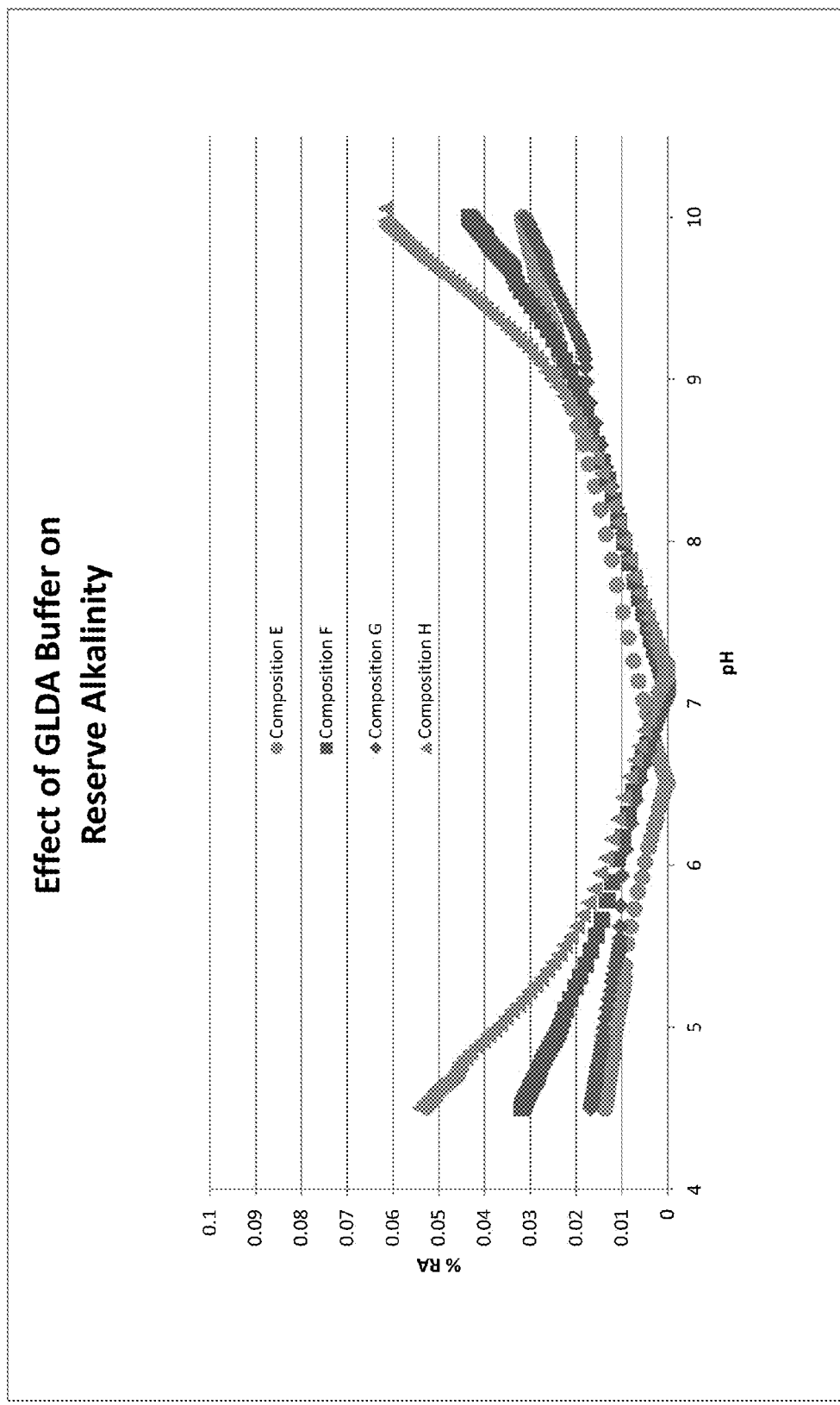
FIG. 6 shows the malodor removal capacity of perfume-free compositions with a GLDA buffer according to the present invention.

FIG. 6 shows that Compositions F, G, and H having GLDA have the capacity to neutralize more malodor, such as butylamine (which is present in fish odors), vs. Composition E, which does not contain GLDA. This increased malodor removal capacity translates to speed of malodor removal.

TABLE 3

| | Composition E | Composition F | Composition G | Composition H |
|---|---|---|---|---|
| DI Water | to 100 | to 100 | to 100 | to 100 |
| Ethanol | 3 | 3 | 3 | 3 |
| DEG | 0.175 | 0.175 | 0.175 | 0.175 |
| Silwet L-7600 | 0.1 | 0.1 | 0.1 | 0.1 |
| Uniquat 2250 | 0.06 | 0.06 | 0.06 | 0.06 |
| Citric Acid | 0.015 | 0.015 | 0.011 | 0.037 |
| Perfume | 0.118 | 0.118 | 0.118 | 0.118 |
| HCO | 0.05 | 0.05 | 0.05 | 0.05 |
| Hydroxypropyl Beta CD | 0.63 | 0.63 | 0.63 | 0.63 |
| Koralone B-119 | 0.015 | 0.015 | 0.015 | 0.015 |
| GLDA | 0 | 0.25 | 0.15 | 0.5 |
| Sodium Hydroxide *adjust to pH 6.8 | 0.002* | 0.002* | 0.002* | 0.002* |
| Maleic Acid | 0.05 | 0.115 | 0.115 | 0.115 |
| Lupasol HF | 0.053 | 0.053 | 0.053 | 0.053 |
| TOTAL | 100 | 100 | 100 | 100 |

All percentages stated herein are by weight unless otherwise specified. It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were=expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A perfume-free composition for reducing malodor comprising:
    an effective amount of a malodor binding polymer;
    an effective amount of a malodor counteractant;
    an aqueous carrier;
    wherein said composition is free of a perfume material and essentially free of any material that would soil or stain fabric.

2. The composition of claim 1 wherein said malodor binding polymer is a polyamine having a molecular weight of at least 150 Daltons and 15% to 80% primary amino groups.

3. The composition of claim 1 wherein said malodor binding polymer is a homopolymeric polyethyleneimine having a molecular weight of about 1,000 to about 2,000,000 Daltons.

4. The composition of claim 3 wherein said homopolymeric polyethyleneimine is present in an amount from about 0.01% to about 0.07%, by weight of said composition.

5. The composition of claim 1 wherein said malodor binding polymer is a homopolymeric polyethyleneimine having a molecular weight of about 25,000 Daltons.

6. The composition of claim 1 wherein said malodor binding polymer is present in an amount from about 0.01% to about 1%, by weight of said composition.

7. The composition of claim 1 wherein said composition further comprises a buffering agent selected from the group consisting of carboxylic acid, dicarboxylic acid, N-(2-Acetamido)-2-aminoethanesulfonic acid, glutamic acid diacetic acid, and mixtures thereof.

8. The composition of claim 1 wherein said composition further comprises glutamic acid diacetic acid.

9. The composition of claim 1 wherein said composition comprises a pH of about 3 to about 10.

10. The composition of claim 1 wherein said composition comprises a pH of about 5 to 8.

11. The composition of claim 1 wherein said composition is free of anionic surfactants.

12. The composition of claim 1 wherein said composition comprises no more than 3% surfactant by weight of said composition.

13. The composition of claim 1 wherein said composition comprises no more than about 1% surfactant by weight of said composition.

14. The composition of claim 1 wherein said composition comprises no more than about 0.5% surfactant by weight of said composition.

15. The composition of claim 1 wherein said aqueous carrier is present in an amount from 90% to about 99.5%.

16. An aqueous perfume-free composition for reducing malodor comprising:
    about 0.01% to about 1%, by weight of said composition, of a homopolymeric polyethyleneimine having a molecular weight of 1,000 to 2,000,000;
    an effective amount of a glycol;
    about 0.15% to about 1%, by weight of said composition, of glutamic acid diacetic acid;
    about 90% to about 99.5% of an aqueous carrier;
    wherein said composition is free of a perfume material and essentially free of any material that would soil or stain fabric.

17. A method of reducing malodor comprising the steps of:
    a. providing the perfume-free composition of claim 1;
    b. dispersing an effective amount of said composition on an inanimate surface or in the air.

* * * * *